(12) United States Patent
Lee et al.

(10) Patent No.: US 7,932,057 B2
(45) Date of Patent: Apr. 26, 2011

(54) METHOD FOR PREPARING 20-O-β-D-GLUCOPYRANOSYL-20(S)-PROTOPANAXADIOL (GINSENOSIDE M1) BY USING SANQI LEAVES AND STEMS

(75) Inventors: Sheau-Long Lee, Longtan Township, Taoyuan County (TW); Yu-Chieh Lee, Longtan Township, Taoyuan County (TW)

(73) Assignee: Sheau-Long Lee, Longtan Township (TW)

( * ) Notice: Subject to any disclaimer, the term of this patent is extended or adjusted under 35 U.S.C. 154(b) by 627 days.

(21) Appl. No.: 11/822,627

(22) Filed: Jul. 9, 2007

(65) Prior Publication Data

US 2009/0017504 A1 Jan. 15, 2009

(51) Int. Cl.
*C12P 19/44* (2006.01)
(52) U.S. Cl. ............................. 435/74; 435/52; 435/171
(58) Field of Classification Search ............... 435/52, 435/74, 171
See application file for complete search history.

(56) References Cited

FOREIGN PATENT DOCUMENTS

TW          I280982 B   *   5/2007

OTHER PUBLICATIONS

Zhang "Assay of total glycoside in San Qi (Panax notoginseng) and its preparation with macroreticular resins" Zhongcaoyao (1981) 12(11): 503-505 (abstract only).*
San Qi from Chinese Medicine Tools downloaded from tcm.health-infor.org/Herbology.Materia.Medica/sanqi-properties.htm on Aug. 25, 2009.*
Du et al. "Synthesis of oligosaccharide derivatives related to those from sanqi, a Chinese herbal medicine from Panax notoginseng" Carb. Res 337 (2002): 485-491.*
Printout from the Registry file showing the strucutre of Panaxzadiol. downloaded from STN on Aug. 26, 2009.*
English translation of TW I280982 downloaded from Google translations on Aug. 6, 2010, 7 pages.*
STN CAPLUS abstract for TW 280982 down loaded from CAPLUS Aug. 12, 2010, 1 page.*

* cited by examiner

*Primary Examiner* — Irene Marx
*Assistant Examiner* — Susan Hanley
(74) *Attorney, Agent, or Firm* — Birch, Stewart, Kolasch & Birch, LLP

(57) ABSTRACT

The present invention provides a method for preparing 20-O-β-D-glucopyranosyl-20(S)-protopanaxadiol (Ginsenoside M1) by using Sanqis leaves and stems. The method of the invention includes the steps of: (a) provides powder of Sanqi leaves and stems; (b) provides a fungus for fermenting the Sanqi leaves and stems, wherein the fermentation temperature is ranged from 20-50° C., the fermentation humidity is ranged from 70-100%, the pH value is ranged from 4.0-6.0, and the fermentation period is ranged from 5-15 days; (c) extracts and collects the fermentation products; and (d) isolates 20-O-β-D-glucopyranosyl-20(S)-protopanaxadiol from the fermentation products.

4 Claims, 8 Drawing Sheets

METHOD FOR PREPARING 20-O-β-D-GLUCOPYRANOSYL-20(S)-PROTOPANAXADIOL (GINSENOSIDE M1) BY USING SANQI LEAVES AND STEMS

BACKGROUND OF THE INVENTION

1. Field of the Invention

The present invention relates to a method for preparing 20-O-β-D-glucopyranosyl-20(S)-protopanaxadiol by using powder of Sanqi leaves and stems, and more particularly, to a method for preparing 20-O-β-D-glucopyranosyl-20(S)-protopanaxadiol from powder of Sanqi leaves and stems derived through fungi fermentation.

2. Description of the Prior Art

According to current studies, after taken by human beings, Panaxadiol can be degraded by enzymes secreted by intestinal microflora to 20-O-β-D-glucopyranosyl-20(S)-protopanaxadiol (so-called Ginsenoside M1, also known as Compound K), which possesses anti-cancer function. Applicant had previously filed an application of a method for preparing 20-O-β-D-glucopyranosyl-20(S)-protopanaxadiol from powder of Sanqi roots through fungi fermentation (Taiwan Patent of Invention No. I 280982), which provides an easier process that is lower in cost with higher yields. Furthermore, the method of the above-mentioned application can improve the methods for preparing 20-O-β-D-glucopyranosyl-20(S)-protopanaxadiol by Naringin enzyme (Chem Pharm Bull 21(3):245-249, 1988) or Helix Snailase (China patent application No. 01133410.X, 06 Nov. 2001, by Yang Ling, et al.). In consideration of the improvement that can be made to promote the prior arts and the need of the industry, applicant continuously studies the related topics and invents the method for preparing 20-O-β-D-glucopyranosyl-20(S)-protopanaxadiol by using powder of Sanqi leaves and stems. Furthermore, through the method of the application, the cost of preparing 20-O-β-D-glucopyranosyl-20(S)-protopanaxadiol can be reduced and the yields of 20-O-β-D-glucopyranosyl-20(S)-protopanaxadiol can be increased by about 10%.

SUMMARY OF THE INVENTION

The present invention provides a method for preparing 20-O-β-D-glucopyranosyl-20(S)-protopanaxadiol by using powder of Sanqi leaves and stems. According to a preferred embodiment of the invention, the method includes the steps of: (a) provides powder of Sanqi leaves and stems; (b) provides a fungus for fermenting the Sanqi leaves and stems, wherein the fermentation temperature is ranged from 20-50° C., the fermentation humidity is ranged from 70-100%, the pH value is ranged from 4.0-6.0, and the fermentation period is ranged from 5-15 days; (c) extracts and collects the fermentation products; and (d) isolates 20-O-β-D-glucopyranosyl-20(S)-protopanaxadiol from the fermentation products.

In an embodiment, fungus preferred is SP-LSL-001.
In an embodiment, the powder of Sanqi leaves and stems is provided for the fermentation.
In an embodiment, the ratio of the weight of the powder of the Sanqi leaves and stems to the weight of the fungus is ranged from 1,000:1 to 10,000:1.
In an embodiment, the fermentation preferred is solid fermentation.
In an embodiment, the fermentation temperature preferred range is from 20-50° C.
In an embodiment, the pH value is preferred range is from 4.0-6.0.
In an embodiment, the fermentation period preferred range is from 5-15 days.
In an embodiment, the fermentation products in step (c) are extracted by ethanol.
In an embodiment, the 20-O-β-D-glucopyranosyl-20(S)-protopanaxadiol in step (d) is isolated by columns.

Another aspect of the invention is to provides a method for transforming Panaxadiol to 20-O-β-D-glucopyranosyl-20(S)-protopanaxadiol. The method includes the steps of: (a) provides powder of Sanqi leaves and stems; (b) provides a fungus for fermenting the Sanqi leaves and stems, wherein the fermentation temperature is ranged from 20-50° C., the fermentation humidity is ranged from 70-100%, the pH value is ranged from 4.0-6.0, and the fermentation period is ranged from 5-15 days; (c) extracts and collects the fermentation products; and (d) isolates 20-O-β-D-glucopyranosyl-20(S)-protopanaxadiol from the fermentation products.

In an embodiment, the Panaxadiol is selected from saponines of stems and leaves of Sanqi, which contain Panaxadiol such as Rb1 and Rb3.
In an embodiment, the fungus used is SP-LSL-001.
In an embodiment, the fermentation temperature preferred range from 20-50 ° C.
In an embodiment, the fermentation humidity preferred range from 70-100%.
In an embodiment, the pH value preferred range from 4.0-6.0.
In an embodiment, the fermentation period preferred range from 5-15 days.
In an embodiment, the fermentation products in step (c) are extracted by ethanol.
In an embodiment, the 20-O-β-D-glucopyranosyl-20(S)-protopanaxadiol in step (d) is isolated by columns.

BRIEF DESCRIPTION OF THE APPENDED DRAWINGS

DETAILED DESCRIPTION OF THE INVENTION

To provide simple, convenient, low-cost and high-yield preparation of 20-O-β-D-glucopyranosyl-20(S)-protopanaxadiol (so-called Compound K, CK), the applicant developed a method for preparing 20-O-β-D-glucopyranosyl-20(S)-protopanaxadiol by using powder of Sanqi leaves and stems.

Figure 1:
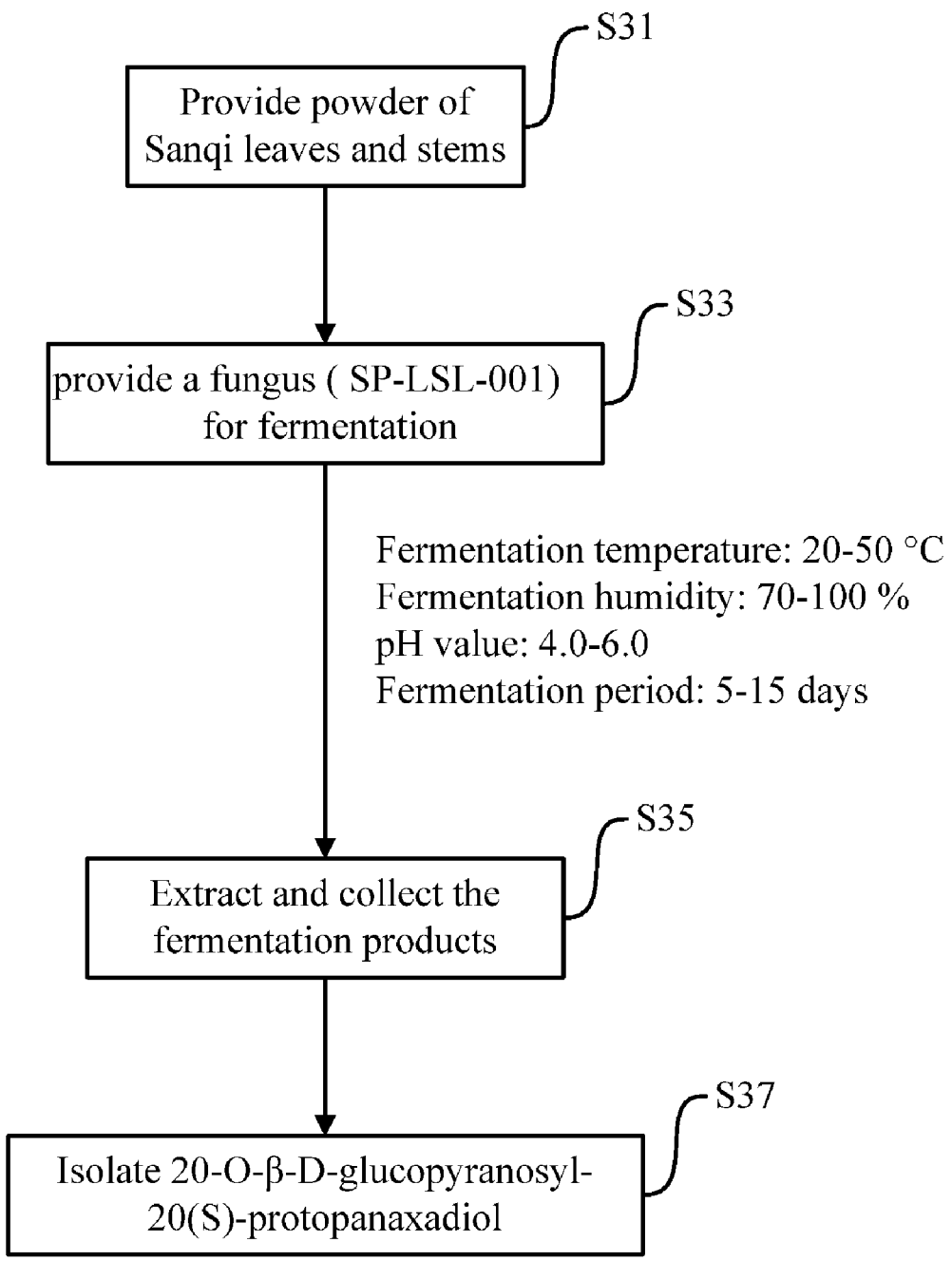
FIG. 1 depicts the steps of the method of the preferred embodiment of the invention.

Please refer to FIG. 1, which shows the method of the preferred embodiment of the invention. As shown in FIG. 1, the method includes the steps of: step S31, provides powder of Sanqi leaves and stems; step S33, provides a fungus for fermenting the Sanqi leaves and stems, wherein the fermentation temperature is ranged from 20-50° C., the fermentation humidity is ranged from 70-100%, the pH value is ranged from 4.0-6.0, and the fermentation period is ranged from 5-15 days; step S35, extracts and collects the fermentation products; and step S37, isolates 20-O-β-D-glucopyranosyl-20(S)-protopanaxadiol from the fermentation products. Because the powder of Sanqi leaves and stems contains Panaxadiol such as Ginsenoside Rb1 and Rb3, the functional groups of Panaxadiol can be metabolize to form 20-O-β-D-glucopyranosyl-20(S)-protopanaxadiol when the powder of Sanqi leaves and stems is fermented with fungus SP-LSL-001.

In a preferred embodiment of the invention, the powder of Sanqi leaves and stems is applied in solid fermentation, to prepare 20-O-β-D-glucopyranosyl-20(S)-protopanaxadiol. Moreover, the process of the solid fermentation is described as follows: first of all, mix the powder of Sanqi leaves and stems with a suitable amount of wheat bran and water. Afterward, sterilizes the mixture under high temperature and high pressure and fills the mixture in a plate after cooling. Finally, embeds the fungus SP-LSL-001.

According to the invention, the preferred fermentation conditions are pH value is ranged from 4.0 to 6.0, fermentation temperature is ranged from 20 to 50° C., humidity is ranged from 70 to 100%, and fermentation period is ranged from 5 to 15 days. Moreover, according to the invention, the preferred ratio of the weight of the powder of the Sanqi leaves and stems to the weight of the fungus is ranged from 1,000:1 to 10,000:1.

In a preferred embodiment of the invention, after the powder of Sanqi leaves and stems is fermented with fungus SP-LSL-001 under the above-mentioned conditions, the fermentation products are extracted by ethanol, and the extraction is concentrated to 30% by distillation and then collected. Afterward, the extraction solution is filtered through macroporous resin, anion exchange resin, and reverse phase chromatography, to obtain 20-O-β-D-glucopyranosyl-20(S)-protopanaxadiol with a purity higher than 95%.

Fungus SP-LSL-001 was deposited on Mar. 25, 1994, in the Biosource Collection and Research Center (BCRC) of the Food Industry Research and Development Institute, 331 Shih-Pin Road, Hsinchu 300, Taiwan, under the accession number BCRC 930079. The Fungus SP-LSL-001 was identified by the Food Industry Research and Development Institute as Aspergillus niger according to the procedure of Raper & Fennell. The identification was based upon an SP-LSL-001 sample provided to the Institute on Sep. 6, 2004, see Report No. 93ID069 SP-LSL-001 which issued on Dec. 1, 2004, to Applicant Sheau-Long Lee.

EXAMPLES

Example 1

To further describe the invention, the applicant performs the experiment as follows: first of all, solid ferments 100 g of the powder of Sanqi leaves and stems with the fungus (wherein the ratio of the weight of the powder of the Sanqi leaves and stems to the weight of the fungus is 1,000:1), to prepare 20-O-β-D-glucopyranosyl-20(S)-protopanaxadiol. Moreover, the process of the solid fermentation is described as follows: first of all, mix the powder of Sanqi leaves and stems with a suitable amount of wheat bran and water. Afterward, sterilizes the mixture under high temperature and high pressure and fills the mixture in a plate after cooling. Finally, embeds fungus SP-LSL-001 to perform the solid fermentation. The fermentation conditions are set at pH value 4.5, fermentation temperature 28° C., humidity 90%, and fermentation period 15 days. After the powder of Sanqi leaves and stems is fermented with fungus SP-LSL-001 under the conditions as described above, the fermentation products are then extracted by ethanol, and the extraction solution is distillation and then collected. Afterward, the extraction solution is passed through macroporous resin, anion exchange resin, and reverse phase chromatography, to obtain 20-O-β-D-glucopyranosyl-20(S)-protopanaxadiol with a purity higher than 95%.

Applicant of the invention performs a High Performance Liquid Chromatography (HPLC) to verify the product of the method of the invention.

Figure 2:
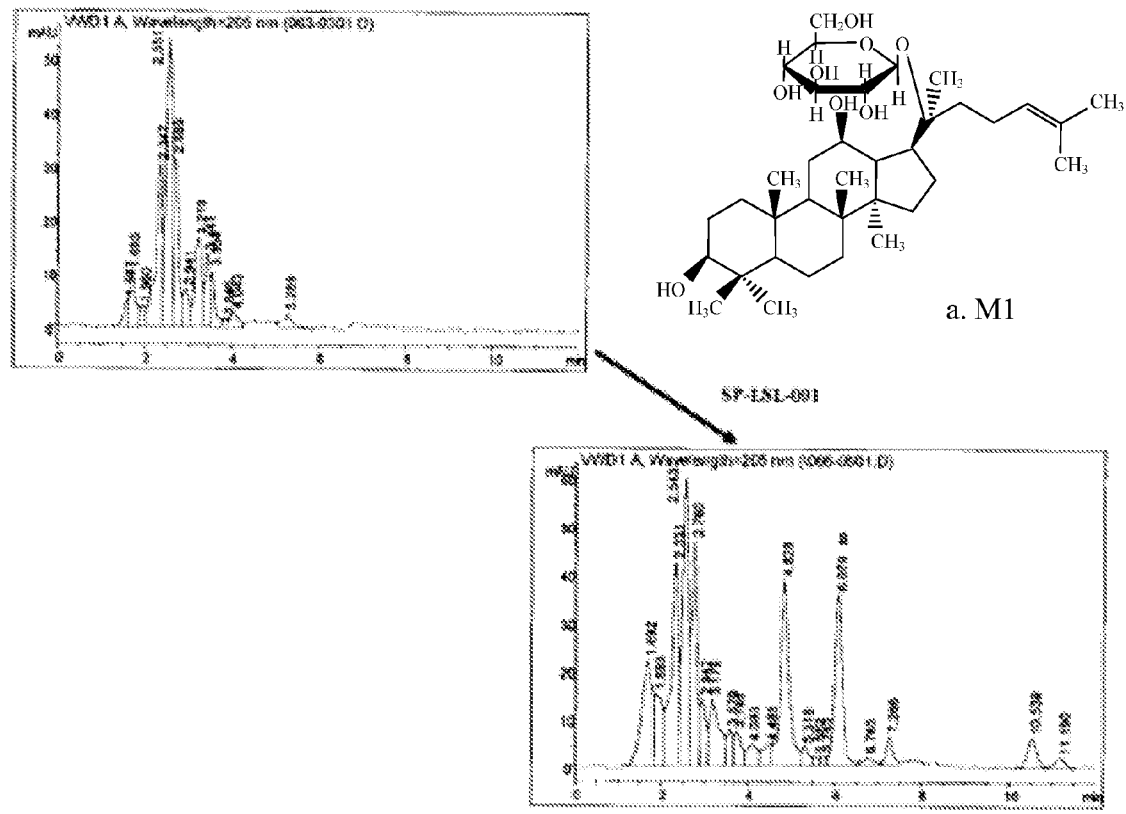
FIG. 2 shows the HPLC result of the composition of the powder of Sanqi leaves and stems before fermentation (upper left part) and the fermentation products after extraction and collection (lower right part).

Please refer to FIG. 2, which shows the HPLC result of the powder of Sanqi leaves and stems before fermentation (upper left part) and the HPLC result of the fermentation products after extraction and collection (lower right part). As shown in FIG. 2, the powder of Sanqi leaves and stems before fermentation did not contain 20-O-β-D-glucopyranosyl-20(S)-protopanaxadiol. On the other hand, the fermentation products after extraction and collection contains 20-O-β-D-glucopyranosyl-20(S)-protopanaxadiol.

According to the above-mentioned method, applicant of the invention develops a method for transforming Panaxadiol to 20-O-β-D-glucopyranosyl-20(S)-protopanaxadiol. The method includes the steps of: (a) provides powder of Sanqi leaves and stems; (b) provides a fungus for fermenting the Sanqi leaves and stems, wherein the fermentation temperature is ranged from 20-50° C., the fermentation humidity is ranged from 70-100%, the pH value is ranged from 4.0-6.0, and the fermentation period is ranged from 5-15 days; (c) extracts and collects fermentation products; and (d) isolates 20-O-β-D-glucopyranosyl-20(S)-protopanaxadiol from the fermentation products.

In a preferred embodiment of the invention, Panaxadiol is selected from Sanqi leaves and stems which is rich in Ginsenoside Rb1 and Rb3, and the fungus used is SP-LSL-001.

Figure 3:
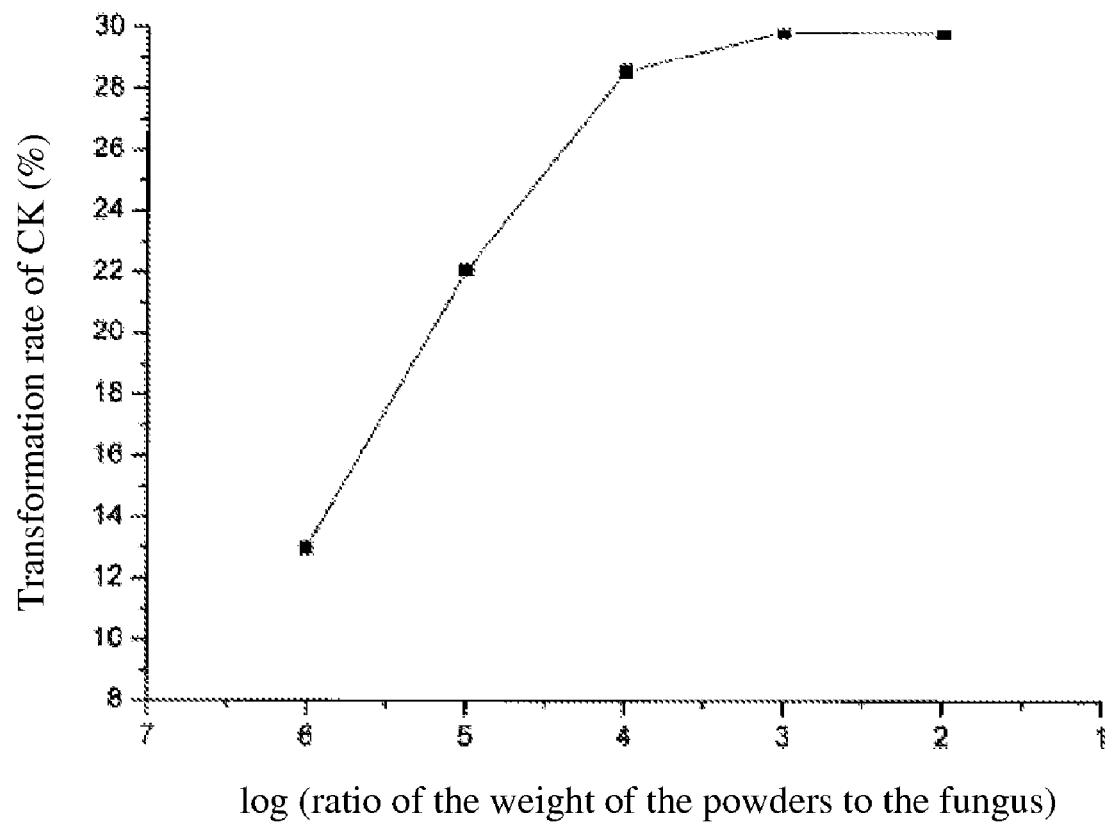
FIG. 3 shows the relationship between the transformation rate of 20-O-β-D-glucopyranosyl-20(S)-protopanaxadiol and the ratio of the weight of the powder of the Sanqi leaves and stems to the weight of the fungus.
Figure 4:
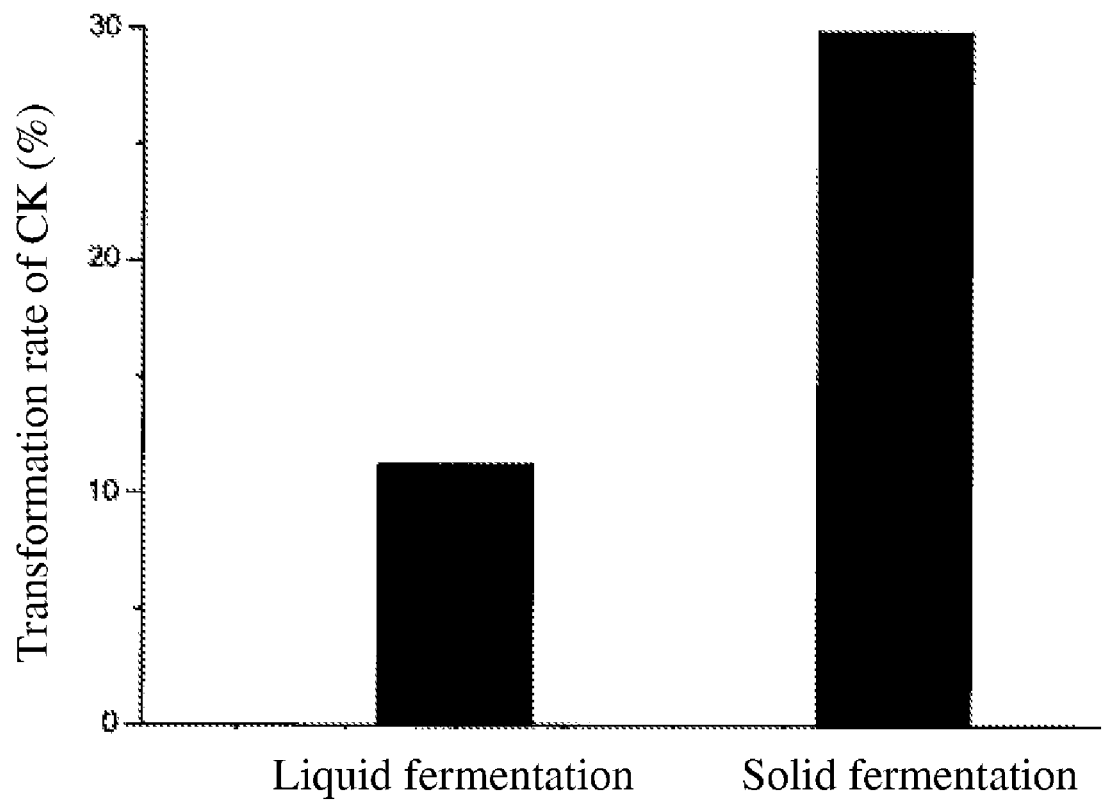
FIG. 4 shows the relationship between the transformation rate of 20-O-β-D-glucopyranosyl-20(S)-protopanaxadiol and the fermentation types (liquid fermentation and solid fermentation).
Figure 5:
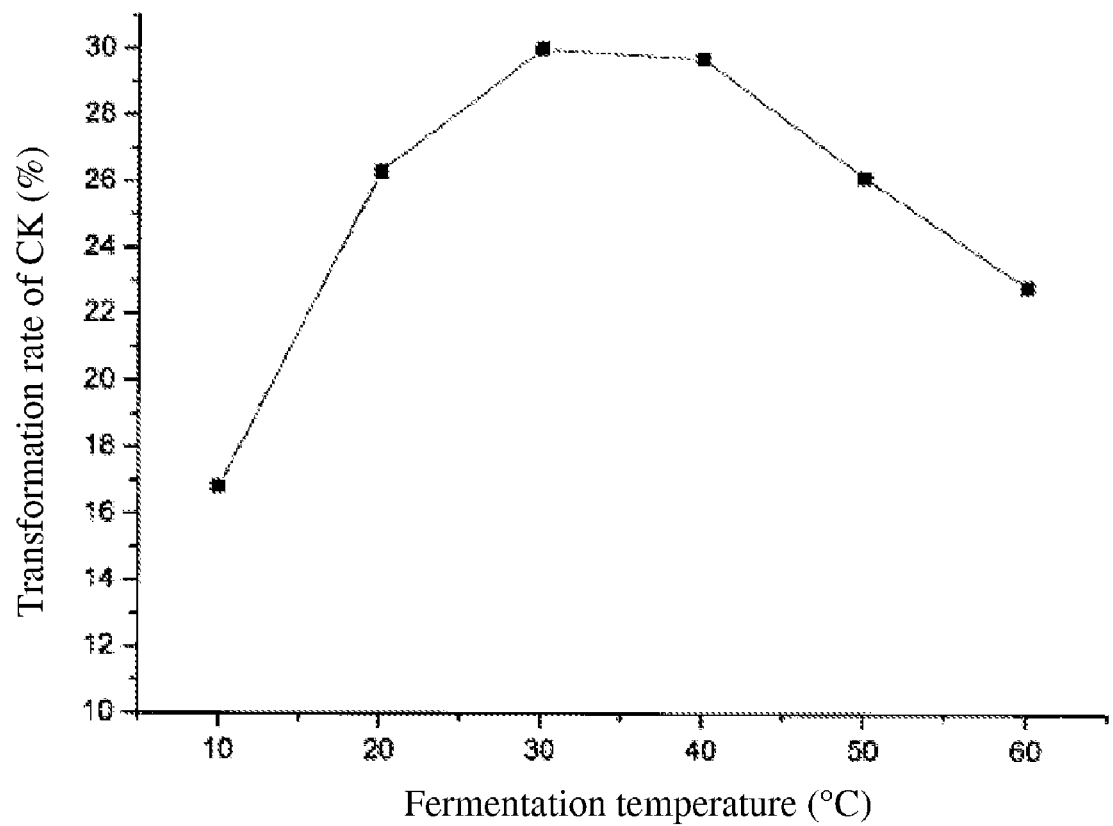
FIG. 5 shows the relationship between the transformation rate of 20-O-β-D-glucopyranosyl-20(S)-protopanaxadiol and the fermentation temperature.
Figure 6:
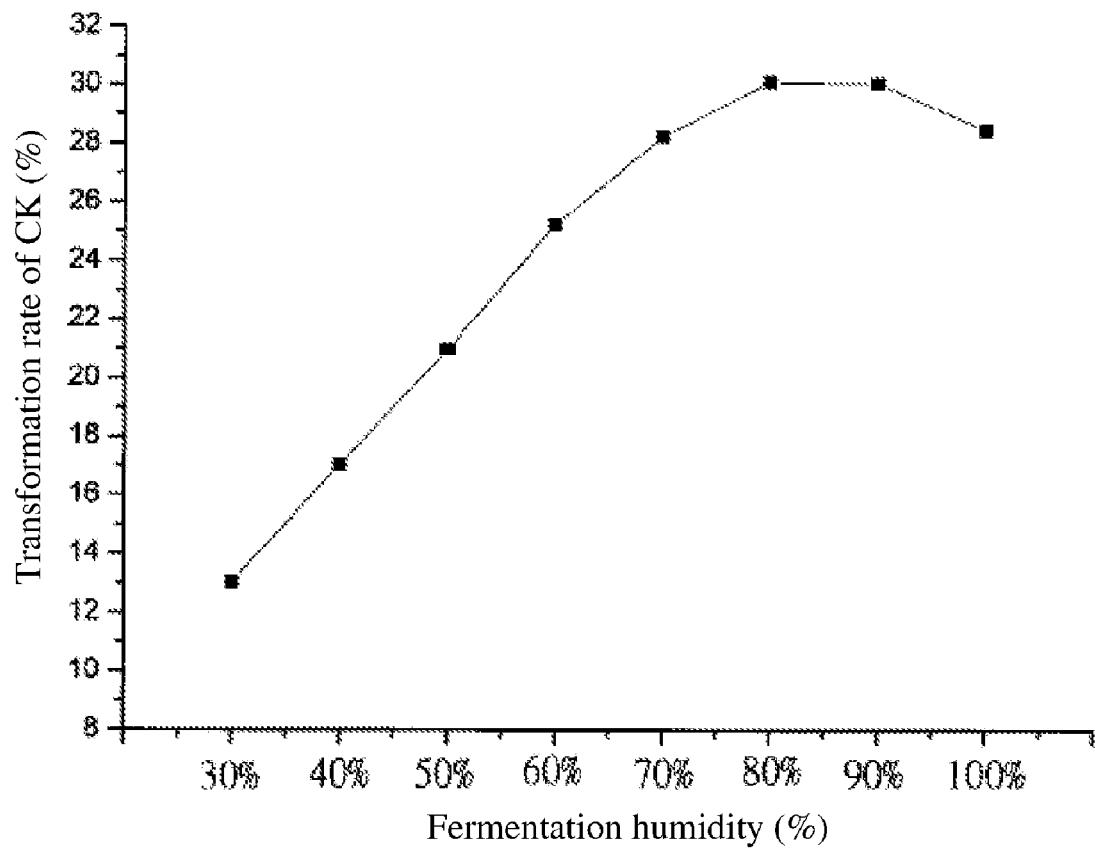
FIG. 6 shows the relationship between the transformation rate of 20-O-β-D-glucopyranosyl-20(S)-protopanaxadiol and the fermentation humidity.
Figure 7:
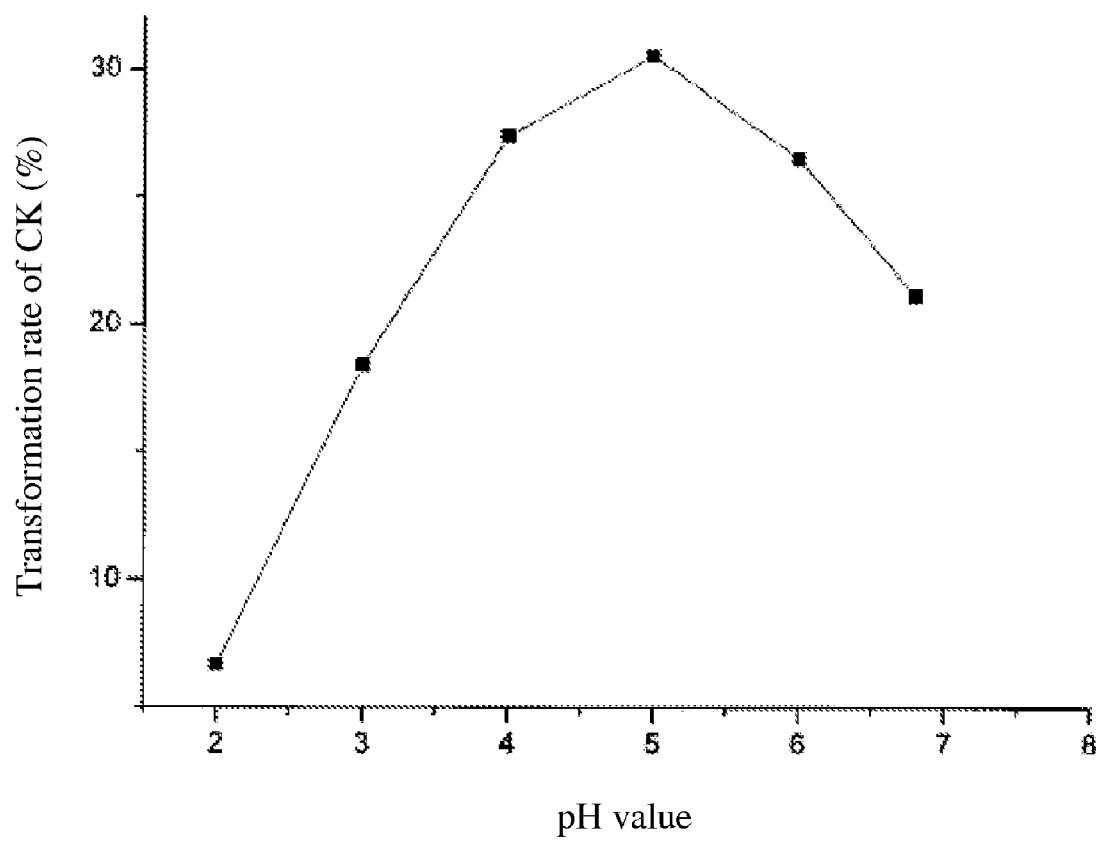
FIG. 7 shows the relationship between the transformation rate of 20-O-β-D-glucopyranosyl-20(S)-protopanaxadiol and the fermentation pH value.
Figure 8:
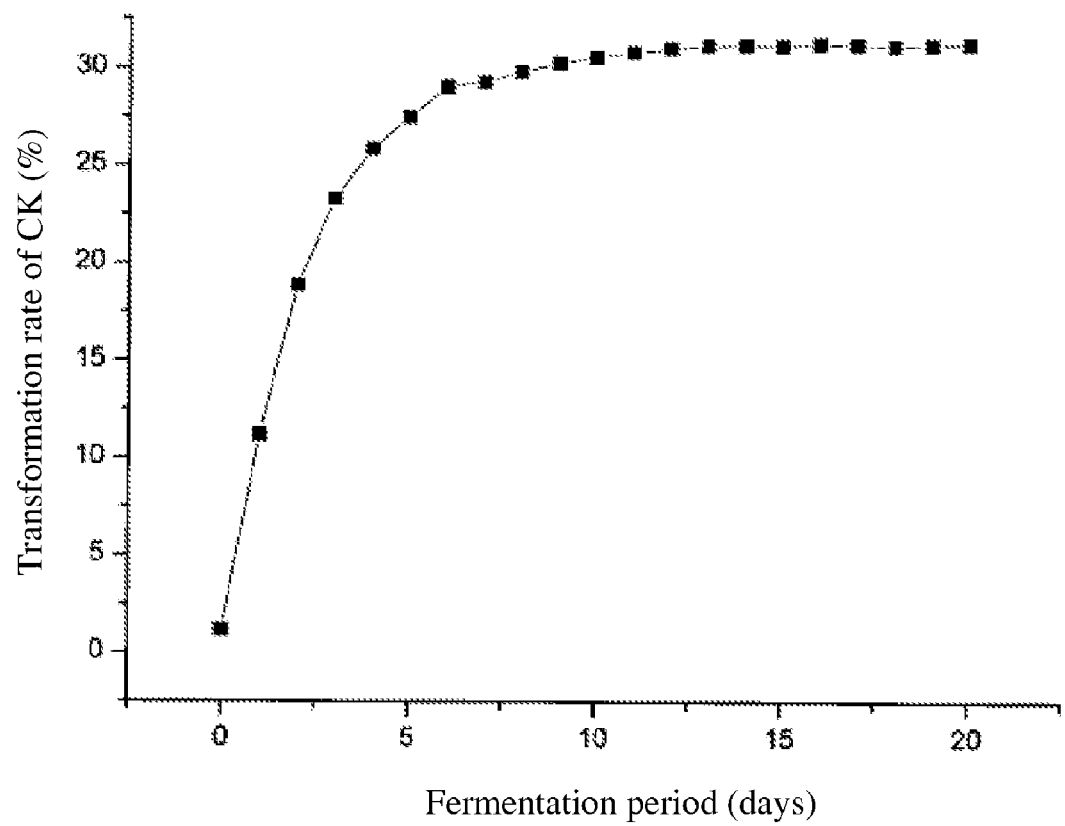
FIG. 8 shows the relationship between the transformation rate of 20-O-β-D-glucopyranosyl-20(S)-protopanaxadiol and the fermentation period.

According to the invention, the preferred fermentation conditions are: pH value is ranged from 4.0 to 6.0 (as shown in FIG. 7), fermentation temperature is ranged from 20 to 50° C. (as shown in FIG. 5), humidity is ranged from 70 to 100% (as shown in FIG. 6), and fermentation period is ranged from 5 to 15 days (as shown in FIG. 8). Furthermore, the preferred ratio of the weight of the power of the Sanqi leaves and stems to the weight of the fungus is ranged from 1,000:1 to 10,000:1 (as shown in FIG. 3). Additionally, as shown in FIG. 4, solid fermentation is better than liquid fermentation for being applied in the invention.

According to the invention, after Panaxadiol is transformed to 20-O-β-D-glucopyranosyl-20(S)-protopanaxadiol, the fermentation products are extracted by ethanol, and the extraction is concentrated to 30% by distillation and then collected. Afterward, the extraction solution is passed through macroporous resin, anion exchange resin, and reverse phase chromatography, to obtain 20-O-β-D-glucopyranosyl-20(S)-protopanaxadiol with high purity.

As described above, the method for preparing 20-O-β-D-glucopyranosyl-20(S)-protopanaxadiol of the invention not only overcomes the disadvantages of the prior arts, but it can also be operated easily. Moreover, the invention has its commercial utility because of the low cost of the powder of Sanqi leaves and stems and the high value and yield of 20-O-β-D-glucopyranosyl-20(S)-protopanaxadiol prepared by the method of the invention.

The invention now being fully described, it will be apparent to one of ordinary skill in the art that many changes and modifications can be made thereto without departing room the spirit or scope of the appended claims.

What is claimed is:

1. A method for preparing 20-O-β-D-glucopyranosyl-20(S)-protopanaxadiol, comprising the steps of:
    (a) providing powder of Sanqi leaves and stems;
    (b) providing a fungus for fermenting the Sanqi leaves and stems;
    (c) fermenting the Sanqi leaves and stems with the fungus to yield fermentation products wherein the fermentation temperature is 20-50° C., the fermentation humidity is 70-100%, the pH value is 4.0-6.0, the fermentation period is 5-15 days, and the fungus is Aspergillus niger, strain SP-LSL-001-deposited as Accession No. BCRC 930079;
    (d) extracting and collecting the fermentation products; and
    (e) isolating 20-O-β-D-glucopyranosyl-20(S)-protopanaxadiol from the fermentation products.

2. The method of claim 1, wherein the ratio of the weight of the power of the Sanqi leaves and stems to the weight of the fungus is 1,000:1 to 10,000:1.

3. The method of claim 1, wherein the fermentation products in step (d) are extracted by ethanol.

4. The method of claim 1, wherein the 20-O-β-D-glucopyranosyl-20(S)-protopanaxadiol in step (e) is isolated by column chromatography.

* * * * *